United States Patent [19]

Kuhn

[11] Patent Number: 4,718,851
[45] Date of Patent: Jan. 12, 1988

[54] HANDPIECE, ESPECIALLY FOR DENTAL PURPOSES

[75] Inventor: Bernhard Kuhn, Schemmerhofen, Fed. Rep. of Germany

[73] Assignee: Kaltenbach & Voigt GmbH & Co., Biberach an der Riss, Fed. Rep. of Germany

[21] Appl. No.: 920,831

[22] Filed: Oct. 17, 1986

[30] Foreign Application Priority Data

Nov. 15, 1985 [DE] Fed. Rep. of Germany ....... 3540621

[51] Int. Cl.$^4$ .............................................. A01C 3/08
[52] U.S. Cl. .................................................. 433/122
[58] Field of Search ................ 433/118, 133, 122, 123

[56] References Cited

U.S. PATENT DOCUMENTS 3,555,685 1/1971 Loge .................................... 433/122
3,578,745 5/1971 Garnier et al. ...................... 433/122

FOREIGN PATENT DOCUMENTS 1552379 2/1972 Fed. Rep. of Germany ...... 433/122

Primary Examiner—Robert Peshock
Attorney, Agent, or Firm—Scully, Scott, Murphy & Presser

[57] ABSTRACT

A handpiece, especially for dental purposes, which is constituted of a gripping sleeve with a treating implement at one end thereof which is supported for limited reciprocating pivotal movement about its axis. The implement is drivable through the utilization of an intermediate drive shaft which is arranged within the gripping sleeve and which is similarly drivable in a limited reciprocable pivoting movement about its axis, whereby for producing the reciprocability of the intermediate drive shaft, the end of the intermediate drive shaft which is distant from the implement cooperates with a wobble surface or swash plate arranged at the end of a drive shaft proxime the implement, which drive shaft is rotatably supported within the handpiece. Moreover, a converting device is arranged between the end of the intermediate drive shaft which is distant from the implement and the swash plate, which converts the rotational movement of the drive shaft into a pivotal movement of the intermediate drive shaft.

10 Claims, 8 Drawing Figures

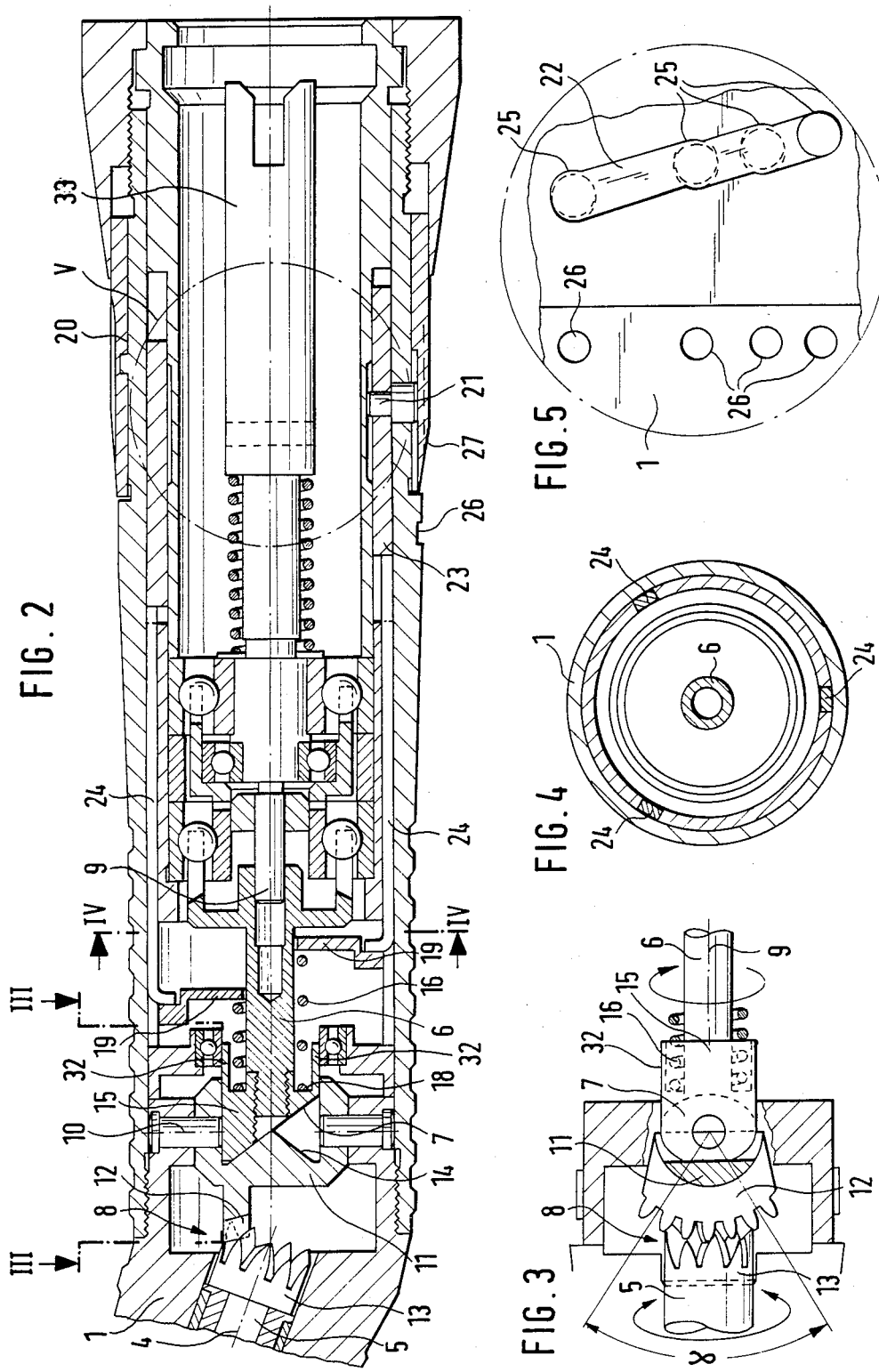

HANDPIECE, ESPECIALLY FOR DENTAL PURPOSES

BACKGROUND OF THE INVENTION

1. Field of the Invention

The present invention relates to a handpiece, especially for dental purposes, which is constituted of a gripping sleeve with a treating implement at one end thereof which is supported for limited reciprocating pivotal movement about its axis. The implement is drivable through the utilization of an intermediate drive shaft which is arranged within the gripping sleeve and which is similarly drivable in a limited reciprocable pivoting movement about its axis, whereby for producing the reciprocability of the intermediate drive shaft, the end of the intermediate drive shaft which is distant from the implement cooperates with a wobble surface or swash plate arranged at the end of a drive shaft proxime the implement, which drive shaft is rotatably supported within the handpiece. Moreover, a converting device is arranged between the end of the intermediate drive shaft which is distant from the implement and the swash plate, which converts the rotational movement of the drive shaft into a pivotal movement of the intermediate drive shaft.

2. Discussion of the Prior Art

A handpiece of this type has become known, for example, from the disclosure of Austrian Patent No. 288 590. In this known handpiece, which is constructed as an angle or elbow member, the converting device is constituted of two parallel, axially displaceable pushers which cooperate with the swash plate, whose ends which are distant from the swash plate alternatingly push against the pressure surfaces in a recess of an angled head of the handpiece receiving the implement, and thereby push with their axes against the similarly angled drive sleeve, constituting in this instance, the intermediate drive shaft.

Independently of the fact, that this known type of construction is employable only for angled and not for straight handpieces, there is also encountered the disadvantage that because of the mentioned pusher arrangement or function, there can be attained only a relatively small pivoting range for the treating implement, such that the tip of the implement effects practically no pivoting or oscillating movement, as a result of which this can then easily lead to a jamming of the implement, especially when the handpiece is utilized for a root-canal treatment, and whereby a release of the jammed implement is almost impossible.

SUMMARY OF THE INVENTION

Accordingly, the invention has as its object to provide a handpiece of the above-mentioned type, in which it is possible to achieve a relatively large pivoting range for the treating implement.

The advantages which are achieved through the present invention can be essentially ascertained in that, especially as a result of the toothed segmented followes and the rooflike engaging element of the intermediate element, there can be achieved a relatively large pivoting angle for the intermediate drive shaft, and resultingly for the treating implement, of about 180°, as a consequence of which there are facilitated pivoting movement at also the tip of the implement.

In addition thereto the handpiece can be constructed as a straight as well as an angled handpiece, since the back and forth or reciprocating pivot movement can be transmitted to the drive shaft within the gripping sleeve either coaxially therewith or somewhat inclined relative to the finally arranged intermediate drive shaft, and is not transmitted to a transversely arranged drive sleeve.

BRIEF DESCRIPTION OF THE DRAWINGS

Reference may now be had to the following detailed description of preferred embodiments of the invention, taken in conjunction with the accompanying drawings; in which:

FIG. 2 illustrates, on an enlarged scale, the portion of the handpiece shown in section in FIG. 1;

FIG. 3 illustrates a sectional view taken along line III—III in FIG. 2;

FIG. 4 illustrates a sectional view taken along line IV—IV in FIG. 2;

FIG. 5 illustrates the encircled portion V in the FIG. 2, in a view facing towards the gripping sleeve.

DETAILED DESCRIPTION

Figure 1:
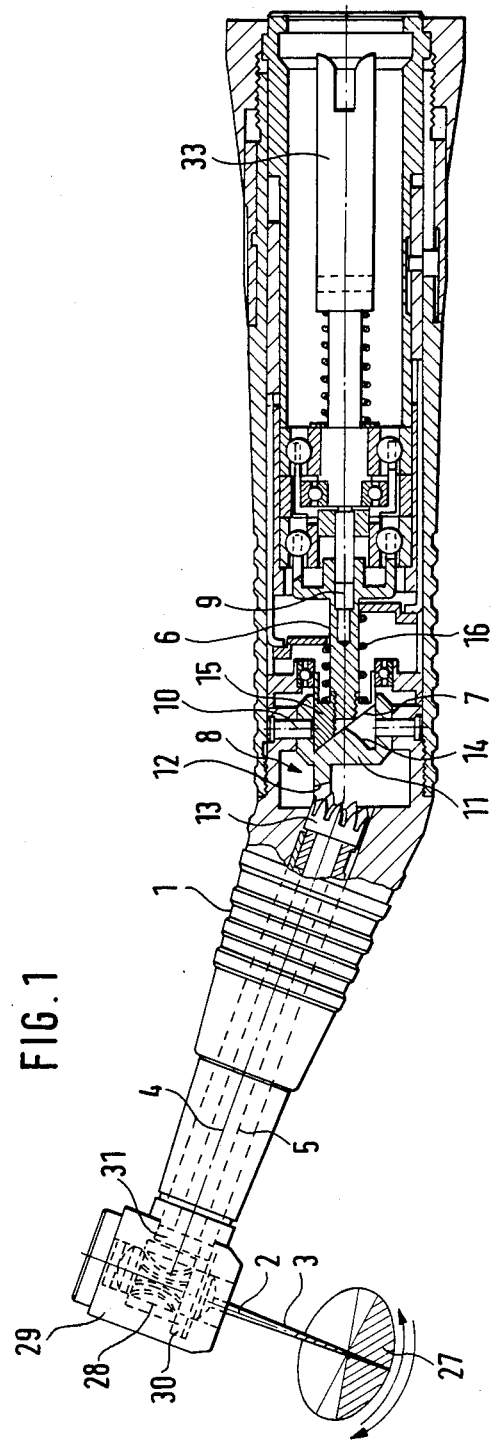
FIG. 1 illustrates a partial side view of the handpiece, shown partly in section.

The illustrated handpiece can serve for medical, and especially dental purposes, and is preferably employed for the root-canal treatment of teeth.

The illustrated handpiece is constructed as an angle or elbow member, and consists of a gripping sleeve 1 with a treating implement 3 at one end thereof which is pivoted for limited reciprocation about its axis 2, whose pivotal range 27 is illustrated by the cross-hatching in FIG. 2. The treating implement 3 is secured against rotation within a drive sleeve 28 which, in turn, is rotatably supported in a head 29 which is angled relative to the gripping sleeve 1. Basically, the implement 3 can also be arranged coaxially with the gripping sleeve 1. However, in the illustrated instance, the drive sleeve 28 possesses a ring gear 30 which engages with a spur gear 31 on the intermediate drive shaft 5 towards the implement. In this manner, can the implement 3 be driven through the intermediate drive shaft 5 which is supported within the gripping sleeve 1 and which is also pivotable within a limited range about its axis 4. In order to achieve the reciprocatable pivotability of the intermediate drive shaft 5, the end of the last-mentioned, which is distant from the implement, cooperates with a wobble surface or swash plate 7 which is arranged on the end of a drive shaft 6 proximate the implement, and which is rotatably supported within the handpiece; wherein a converting device 8 is interposed between the end of the intermediate drive shaft 5 which is distant from the implement and the swash plate 7, so as to translate the continual rotational movement of the drive shaft 6 into a pivoting or oscillating movement of the intermediate drive shaft 5.

In accordance with FIGS. 1 and 2, the drive shaft 6 is provided at the end thereof which is distant from the implement with a follower 33 which is engageable with a drive (not shown); for example, a motor.

Figure 6:
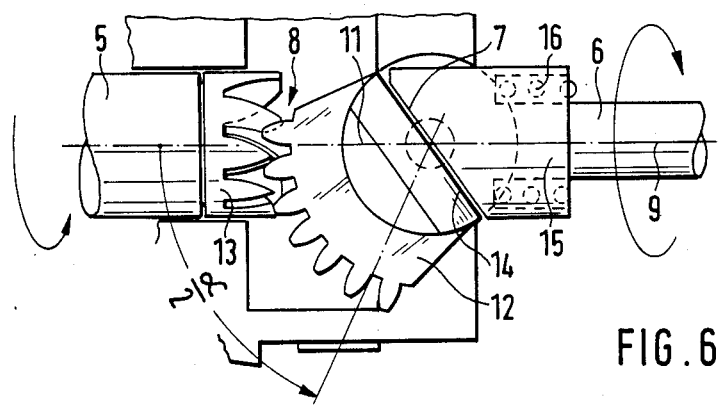
FIGS. 6 through 8, respectively, illustrate the arrangement of FIG. 3 in three different pivoted positions of the intermediate element of the converting device of the handpiece possessing the toothed segmented followes.
Figure 7:
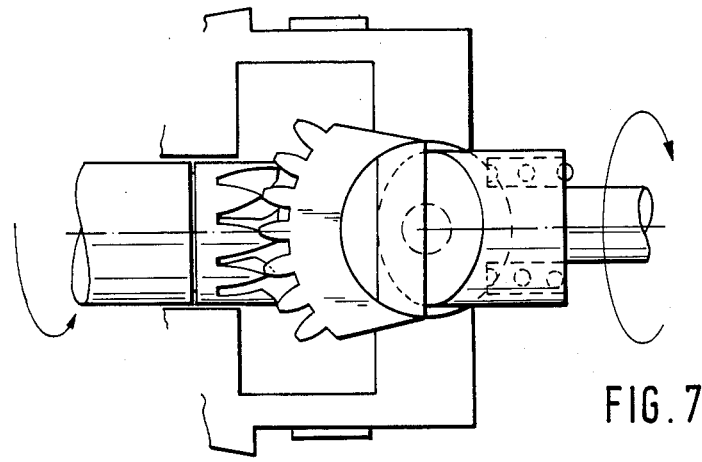
Figure 8:
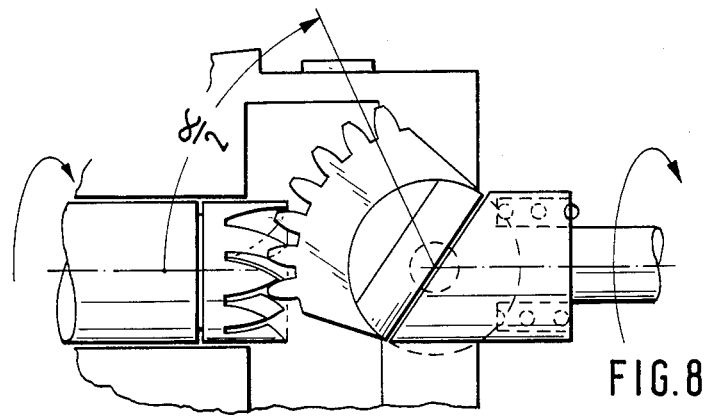

The converting device 8 consists of an intermediate element 11 reciprocably pivotable about the pivot axis 10 and extending transversely of the axis 9 of the drive shaft 6, which is provided with a toothed-segment follower 12 transmitting the reciprocating pivoting movement caused by the wobble surface or swash plate 7 of the drive shaft 6, for the engagement into the spur gear 13 on the intermediate drive shaft 5 distant from the implement; as well as being provided with a rooflike engaging element 14 for cooperation with the swash plate 7, which during the rotation of the drive shaft 6, pivots the engaging element 14 back and forth, and thereby the intermediate element 11. In FIG. 3, the pivoting angle of the intermediate element 11 and, consequently, that of the intermediate drive shaft 5 is identified by α. In FIGS. 6 and 8 there is presently identified the half pivot angle by α/2.

In detail, the wobble surface or swash plate 7 is arranged on a coupling element 15 distant from the drive shaft, which is supported axially movably on the end of the drive shaft 6 towards the implement, and which, for the formation of a slipping clutch, contacts with the wobble surface 7 under the action of a spring 16 against the rooflike engaging element of the intermediate element. The spring 16, which acts as an adjusting spring, is extended over by external axial projections 32 on the coupling element 15. The rooflike engaging element 14 of the intermediate element 11 causes the back and forth movement or pivoting in the described arrangement.

In order to vary the tractive moment of the coupling element 15, the force of the spring 16 can be made adjustable. Hereby, with an implement which is jammed in or clamped in the handpiece, there is furthermore reciprocatably supported up to the present magnitude of the adjusted spring or tractive force, the loosening of the jammed in implement 2.

The spring 16 is constituted of a coiled compression spring which is arranged on a shank portion 17 of the coupling element 15, supported on the one side against an annular projection 18 of the coupling element and on the other side, against an axially movable stop 19 which axially adjustable from the outside. The stop 19 is hereby formed as a ring-shaped plate engaging about the drive shaft 6.

For the axial adjustment of the stop 19, there is provided a turning ring 20 cooperating with the former end rotatably engaging the gripping sleeve 1, which converts a rotational movement into an axial movement, in which the turning ring 20 can be easily manipulated from the outside. The turning ring 20 possesses an inwardly extending projection 21 which engages through an angled slot 22 in the gripping sleeve 1 in the type of a screwline section, and which stands in engagement with an axially displaceable sliding sleeve 23 arranged within the gripping sleeve 1, which sliding sleeve, in turn, is in an operative connection with the stop 19.

Arranged between the sliding sleeve 23 and the stop 19 is at least one adjusting component 24 forming a transmitting element. Pursuant to the embodiment of FIG. 4, there are provided three adjusting components. As shown in the upper half of FIG. 2, the stop 19 is in a position causing a maximum tractive moment, whereas the stop 19 in the lower half of FIG. 2 is located in a position causing a minimum tractive moment.

In accordance with FIG. 5, the angled slot 22 possesses a plurality of detents producing engaging or latching points 25 for the projection 21. The latching points 25 have optical latching indicia 26 associated therewith on the outside of the gripping sleeve 1, wherein the outside of the turning ring 20 is provided with a read-off indicia 27. The latching point illustrated in the upper portion of FIG. 5 conforms with a position of the maximum tractive moment, whereas the lower latching point 25 conforms with a position of the minimum tractive moment.

What is claimed is:

1. Handpiece, especially for dental purposes, comprising a gripping sleeve; a treating implement supported at one end of said gripping sleeve for limited reciprocating pivotal movement about its axis; an intermediate drive shaft for driving said treating implement arranged in the gripping sleeve and being reciprocably pivotable about its axis to a limited extent; wobble surface means for effecting the reciprocable pivotability of said intermediate drive shaft, said wobble surface means being arranged at the end a drive shaft towards said implement which is rotatably supported within the handpiece and operatively cooperating with the end of said intermediate drive shaft which is distant from the implement; converting means arranged between the end of the intermediate drive shaft which is distant from the implement and the wobble surface means for converting the rotational movement of the drive shaft into a pivoting movement of the intermediate drive shaft, said converting means including an intermediate element reciprocably pivotable about a pivoting axis extending transversely of the axis of said drive shaft, a toothed-segment follower on said intermediate element transmitting the reciprocating pivoting movement engaging a spur gear on said intermediate drive shaft, and a rooflike engaging element for cooperation with the wobble surface means of the drive shaft.

2. Handpiece as claimed in claim 1, wherein said wobble plate is arranged at the end of a coupling element which is distant from the drive shaft, said coupling element being axially movably supported on the end of the drive shaft towards the implement, which for the formation of a slipping clutch, under the action of a spring, contacts with the wobble surface means against the rooflike engaging element of the intermediate element.

3. Handpiece as claimed in claim 2, wherein the force of the spring is adjustable for changing the tractive moment of the coupling element.

4. Handpiece as claimed in claim 3, wherein the spring comprises a helical compression spring arranged on a shank portion of the coupling element, and being supported at one end against a ring-shaped projection on the coupling element, and at the other end against an axially movable stop which is axially adjustable from outside the handpiece.

5. Handpiece as claimed in claim 4, wherein the stop comprises an annular plate encompassing the drive shaft.

6. Handpiece as claimed in claim 4, wherein a turning ring facilitates the axial adjustment of the stop cooperates with said stop by converting a rotational movement into an axial movement, said turning ring rotatably encompassing said gripping sleeve.

7. Handpiece as claimed in claim 6, wherein the turning ring includes an inwardly extending projection traversing a screw-like angled slot in the gripping sleeve, and which is in engagement with a sliding sleeve arranged within the gripping sleeve, said sliding sleeve being in an operative connection with the stop.

8. Handpiece as claimed in claim 7, wherein at least one adjusting elbow is arranged between the sliding sleeve and the stop to provide a transmitting element.

9. Handpiece as claimed in claim 7, wherein the angled slot includes a plurality of detents forming latching points for the projection.

10. Handpiece as claimed in claim 9, wherein the latching points have optical latching indicia on the outside of the gripping sleeve associated therewith and wherein read-off indicia is provided on the exterior of the turning ring.

* * * * *